US00PP10043P

United States Patent [19]

Lamb et al.

[11] Patent Number: Plant 10,043

[45] Date of Patent: Sep. 23, 1997

[54] ANTHURIUM PLANT NAMED GEMINI

[75] Inventors: Ann E. Lamb, Sebring; Robert D. Hartman, Lake Placid, both of Fla.

[73] Assignee: Twyford International, Inc., Santa Paula, Calif.

[21] Appl. No.: 629,636

[22] Filed: Apr. 9, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

An Anthurium plant named 'Gemini' having glossy dark pink spathes with a contrasting white and yellow spadix, the spathes being carried above the foliage. The leaves are lanceolate, dark green and shiny. The growth habit is moderately branched and somewhat spreading.

1 Drawing Sheet

1

The present invention comprises a new and distinct cultivar of Anthurium, botanically known as *Anthurium hybrid*, and referred to by the cultivar named 'Gemini'.

The new cultivar is a product of a breeding program carried out by the inventors Ann E. Lamb and Robert D. Hartman in Apopka and Sebring, Fla., and is the result of the following cross made in Apopka in February 1993: Anthurium 'White Aristocrat', disclosed in U.S. Plant Pat. No. 8,821×An unnamed Anthurium hybrid identified by a proprietary code number.

The cultivar was discovered from the progeny of the stated cross in May 1995 by Ann E. Lamb. Tissue culture performed by or under the supervision of Ann E. Lamb at Sebring, Fla. was used to increase the number of plants for evaluation and has demonstrated the stability of the combination of characteristics of 'Gemini' from generation to generation.

The following observations, measurements and values describe plants grown in Homestead, Fla. under shade house conditions which closely approximate those generally used in horticulture practice.

The following traits have been repeatedly observed to be characteristics which in combination distinguish 'Gemini' from other Anthuriums of the same general type, for example, the patented cultivar 'Lady Jane' to which comparative reference is made.

1. The plant produces glossy dark pink spathes, with a contrasting white and yellow spadix, with the spathes being carried above the foliage.

2. The spathes are cupped when first open, and flatten as they age.

3. The leaves are dark green, acutely tapered and have a shiny surface.

4. The plant habit is moderately branched and somewhat spreading.

5. The spathe color actually darkens somewhat as the spathe matures, an important feature to the ultimate consumer.

Compared to 'Lady Jane', 'Gemini' grows to a marketable size in less time. The flowers of 'Gemini' are generally much larger, flatter, and more abundantly produced. In addition, the leaves of 'Gemini' are much longer, narrower, and more tapered compared to those of 'Lady Jane'.

All color references are measured against The Royal Horticultural Society Colour Chart. Colors are approximate as color depends on horticultural practices such as light level and fertilization rate, among others, without, however, any variance in genotype.

The color photographic drawing comprises a top perspective view of the inflorescence and foliage of a plant of

2

'Gemini' in a 15.3 cm pot approximately 10 months after planting a 20 week old liner obtained by tissue culture and grown under appropriate growing conditions.

Colors are as accurate as possible with color illustrations of this type.

Origin: Seedling selected from a cross of Anthurium 'White Aristocrat'×an unnamed hybrid identified by a proprietary code number.

Classification: *Anthurium hybrid*, cv. 'Gemini'.

Propagation: Asexual production either by tissue culture or division.

INFLORESCENCE

Immature: The spathe is tightly rolled around the spadix and emerges from the petiole sheath. The spathe is fully open about when the peduncle is fully elongated, approximately 22.5 cm to 28 cm above the soil surface. The color of the flower peduncle is 144 A. The flower peduncle just below the flower often becomes somewhat anthocyanous, and flushed with 173 A.

Mature:

*Color.*—Fully open: Upper surface: 53 C. Lower surface: 50 B, 51 B. Faded: Upper Surface: 53 B. Lower Surface: 45 D.

*Arrangement.*—The inflorescence terminates from a straight wiry peduncle and opens vertically above the leaves.

*Shape.*—The spathe is ovate with a slightly cordate to truncate base and a cuspidate tip. It is slightly cupped when first open, flattening with age.

*Size.*—The fully expanded spathe is approximately 6.5 cm to 7.7 cm long and approximately 4.5 cm to 5.2 cm in width.

*Flowering time.*—After approximately 10 months from a 20 week old liner for an untreated plant as illustrated in the photograph and depending on season, approximately 6 to 7 blossoms will be present. Smaller blooms may occur on less mature growth. First flowers are typically produced approximately 3–4 months after planting a 20 week old liner. Approximately 3 flowers are present.

REPRODUCTIVE ORGANS

Spadix:

*Size.*—Approximately 4.0 cm to 4.3 cm in height and approximately 7 mm in width.

*Color.*—When the spathe unrolls, the spadix is 155 A, with 11 B, 150 C at the tip. The spadix develops a green 145 B cast with age.

*Stamens.*—Anthers and filaments are minute and not clearly visible. Pollen is white in color.

*Pistil.*—Translucent white, protruding between the staminate flowers, firmly fixed to the main axil. The pistilate flowers extend approximately 0.7 mm beyond the staminate flowers.

General appearance: Under appropriate growing conditions, 'Gemini' reaches a marketable size of approximately 22 cm to 26 cm in height and approximately 52 cm to 60 cm in width.

Leaves:

*Form.*—The leaf blade is ovate or lanceolate with a distinctly tapered acute tip and an obtuse or truncate base. The midrib is straight over the length of the leaf, and curved downward at the tip. The leaf margins are straight or slightly wavy.

*Size.*—Leaf blades of a mature sized plant are approximately 18.0 cm to 22 cm in length and approximately 11.2 cm to 13.3 cm in width.

*Veins.*—The veins are sunken, with the leaf blade slightly convex between veins on the upper surface. The midrib protrudes from the upper surface of the leaf for approximately ¾ the length of the leaf. Well defined primary veins on leaves radiate out from the juncture of the petiole and the leaf. Veins stand out prominently on the lower side. There are approximately 4–6 primary veins on the leaf.

*Petiole.*—The petiole is approximately 16.8 cm to 20.5 cm in height from the base of the petiole to the base of the leaf blade on the primary shoot. The petiole is approximately 3.5 mm in diameter just below the geniculum. The petiole below the geniculum is straight. Secondary shoots are somewhat smaller depending on the age of the shoot.

*Petiole wings.*—Petiole wings are approximately 2.2 cm in length and approximately 2.5 mm in width at their midpoint. The tip of the petiole wings is rounded. There is approximately 11 cm between the top of the wing and the base of the geniculum.

*Geniculum.*—The geniculum is approximately 3.2 cm to 3.8 cm in length, approximately 4.5 mm in diameter, and is often curved. There is no space between the top of the geniculum and the base of the leaf blade.

*Lobes.*—The leaf has two rounded lobes which do not extend past the petiole. The distance from the petiole/leaf juncture to the highest point on the lobes is approximately 5.7 cm to 6.5 cm.

*Colors.*—Upper surface: Much darker and greener than, but closest to, 147 A. Lower surface: 146 B. Midrib, upper surface: 146 B. Midrib, lower surface: 145 A. Petiole: 144 A. Petiole wing: 144 A-B. Geniculum: 144 A.

Roots: White fleshy roots with fine laterals.

We claim:

1. A new and distinct cultivar of Anthurium plant named 'Gemini', as illustrated and described.

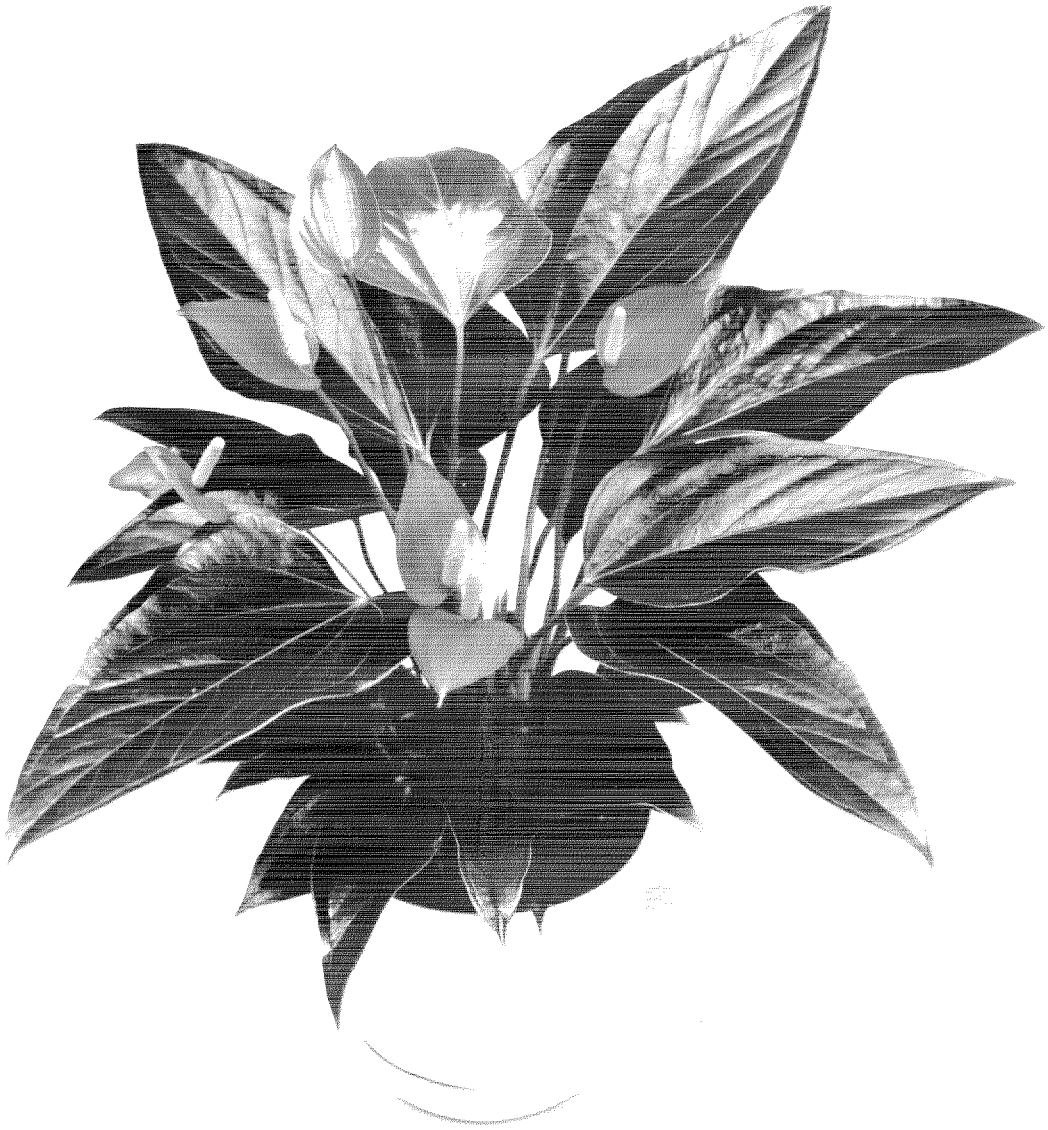

* * * * *